United States Patent [19]

Gulliya et al.

[11] Patent Number: 5,091,385
[45] Date of Patent: Feb. 25, 1992

[54] PRE-ACTIVATED THERAPEUTIC AGENTS DERIVED FROM PHOTOACTIVE COMPOUNDS

[75] Inventors: Kirpal S. Gulliya; Shazib Pervaiz; J. Lester Matthews; Robert M. Dowben; Joseph T. Newman; Edward Forest, all of Dallas, Tex.

[73] Assignee: Baylor Research Institute, Dallas, Tex.

[21] Appl. No.: 252,256

[22] Filed: Sep. 30, 1988

[51] Int. Cl.[5] .................. A61K 31/47; A61K 31/535; A61K 31/54
[52] U.S. Cl. ......................... 514/224.8; 204/157.72; 514/229.8; 514/250; 514/270; 514/274; 514/297; 514/314; 514/367; 514/410; 514/414; 514/415; 514/638; 514/150
[58] Field of Search ...................... 514/270, 150, 224.8, 514/229.8, 250, 274, 297, 314, 367, 410, 414, 415, 638

[56] References Cited

U.S. PATENT DOCUMENTS 4,649,151 3/1987 Dougherty et al. ................ 514/410

OTHER PUBLICATIONS

Gulliya et al, Photochemistry and Photobiology, vol. 52, No. 4, (1990) pp. 831–838.

*Primary Examiner*—Richard L. Raymond
*Attorney, Agent, or Firm*—Cox & Smith, Inc.

[57] ABSTRACT

A pre-activated therapeutic agent derived from a photoactive compound for destroying tumor or other pathogenic biological contaminants infecting animal body tissues. The activation of the photoactive compound is carried out prior to the photoactive compound is being brought into contact with the tissue to be treated. The resultant pre-activated therapeutic agent, or mixture, retains its therapeutic activity subsequent to activation. A method for preparing such a pre-activated therapeutic agent is disclosed. Methods for treating animal body tissue, either outside the body or inside the body, infected with tumors or other pathogenic biological contaminants are disclosed.

35 Claims, No Drawings

PRE-ACTIVATED THERAPEUTIC AGENTS DERIVED FROM PHOTOACTIVE COMPOUNDS

FIELD OF INVENTION

The present invention relates generally to pre-activated therapeutic agents derived from photoactive compounds and more particularly to methods, compositions, and solutions for destroying tumor cells or other pathogenic biological contaminants in body tissues. One method of the present invention includes treating body tissues, which are infected with tumor or other pathogenic biological contaminants, either inside the animal body, such as human body, or outside the animal body.

BACKGROUND OF THE INVENTION

Photodynamic therapy (PDT) is an ancient concept and has been described and utilized over 30 centuries ago. The therapy was used in ancient times for the treatment of vitiligo in India, China and Egypt. In the last century, ultraviolet (UV) radiation was successfully used in the treatment of lupus vulgaris, a type of skin tuberculosis endemic in the Scandinavian countries.

PDT usually involves the administration of one or more photoactive agents to the subject to be treated followed by exposing the specific target location or target organ of the subject to light. Thus, for example, upon illumination, Methylene Blue has been used to kill *Trichoderma viride*, a common fungus, outside the body. Similarly, acridine orange, as well as Methylene Blue, kills blood fluke *Schistosoma mansoni*, in vitro, upon exposure to light. P. S. Lacaz and J. C. E. Holanda, Bol. Acad. Nac. Med. (Brazil) 145: 43 (1974), Chem Abstr. 86:134166. Likewise, larvae of Anopheles mosquitoes are killed by the simultaneous exposure to photoactive dyes and light. A. Barbieri, Accion fotodynamica de la luz. Riv. Malariol, 7: 456 (1928); H. Schildmacher, Biol. Zentr. 69: 468 (1950).

PDT has been used to neutralize externally the toxicity of many snake venoms without significantly altering their antigenicity so that they can still be used to manufacture antibodies for the snake venom. W. F. Kocholaty, J. C. Goetz, et al., Toxicon 5: 153 (1968). Similar results have been reported for some animal viruses. Thus, utilizing similar technique, vaccines, including influenza vaccines, have been prepared. J. D. Spikes and R. Livingston, Adv. Radiat. Biol. 3: 29 (1969); C. V. Hanson, in "Medical Virology," Proc. Int'l Symp. 2: 45, Elsevier (1983). Likewise, influenza or encephalomyelitis viruses externally added to contaminate human blood plasma are inactivated by light in the presence of toluidine blue dye without significant alteration to the properties of plasma proteins. F. Heinmets, J. R. Kingston and C. W. Hiatt, Walter Reed Army Institute of Research Report 53-55: 1 (1955).

Extracorporeal PDT, utilizing light and psoralen dyes, has also been reported for the treatment of cutaneous T-cell lymphoma. Psoralen dyes in the presence of light have also been used for the treatment of vitiligo. T. B. Fitzpatrick and M. A. Pathak, J. Invest. Dermatil. 32: 229 (1959); A. V. Benedetto, Cutis 20: 469 (1977). Skin tumors have been treated with the simultaneous exposure of the tumors to both eosin dyes and light. H. V. Tappeiner and A. Jesionek, Munch. Me. Wochenschr. 50:2042 (1903).

In the early 40's, it was observed that hematoporphyrin derivative (hereinafter Hpd) preferentially accumulated in tumors and lymph nodes. H. Auler and G. Banzer, Z. Krebforsch. 53:65 (1942). As a result, methods have been developed to capitalize on the unique property of Hpd as a tumor marker in the detection and localization of different forms of cancer cells. E. G. King, et al., Hematoporphyrin Derivative as a Tumor Marker in the Detection and Localization of Pulmonary Malignancy, in *Recent Results in Cancer Research*, Vol. 82, Springer-Verlag, Berlin-Heidelberg, 1982, 90; R. D. Benson, et al., Mayo Clinic Proc. 57:548 (1982).

Although the unique photodynamic properties of Hpd, as well as its unique preferential affinity toward tumor cells, had long been known, it was more than half a century later that the potential of using Hpd to selectively destroy tumor cells was explored. In 1966, Lipson and co-workers reported treating one case of recurrent breast cancer using a combination of Hpd and light. M. S. Lipson, M. J. Gray and E. J. Baldes, Proc. 9th Intl. Cancer Congr., p. 393 (1966). The use of light in the presence of Hpd to selectively destroy tumor cells in human has been reviewed by Dougherty et. al. T. J.. Dougherty, et al., Photoradiation Therapy: Clinical and Drug Advances. In *Porphyrin Photosensitization*, D. Kessel and T. J. Dougherty, Eds. Plenum Press, N.Y., pp. 3-13, 1983.

U.S. Pat. No. 4,649,151 teaches the preparation and purification of porphyrin-type drugs. The patent also teaches the diagnosis and destruction of cancer cells with porphyrin-type drugs. In treating humans or other mammals with the drugs, light must be irradiated on the cancer cells in such a position as to uniformly illuminate the cancer cells. When cancer cells, having the porphyrin-type drugs associated therewith, are illuminated with light, the drugs are activated and thus causing the destruction of the cancer cells by a mechanism not completely understood yet. The patent also discloses several apparatus for transmitting light to different parts of the body.

U.S. Pat. No. 4,614,190 discloses that while a dye such as Hpd is being held within the tumor cells in the body, the activation of the dye is accomplished by pulsed electromagnetic radiation.

U.S. Pat. No. 4,727,027 teaches the inactivation of pathogenic biological microorganisms by simultaneous treatment with furocoumarins and a long wavelength ultraviolet light under conditions which limit the availability of oxygen and other reactive species.

U.S. Pat. No. 4,684,521 teaches a chemical agent for the reduction of the population of a selected blood constituent having receptor sites. The invention uses a photoactive agent physically incorporate within or chemically bound to a carrier molecule. The carrier molecule has a strong affinity for the receptor sites on the blood constituent. When activated by Ultraviolet ("UV") radiation, the photoactive agent bound to the carrier molecule interferes with the metabolism of the selected blood constituent.

U.S. Pat. No. 4,613,322 discloses a method and system for externally treating human blood to reduce the functioning lymphocyte population in the blood system. According to the method, blood is treated with a photoactive agent and simultaneously irradiated with UV radiation outside the body.

U.S. Pat. No. 4,708,715 teaches a removable UV light array assembly for use in a patient system wherein photoactivatable agents, in contact with patient blood cells, are irradiated extracorporeally and then returned to the patient.

Cyanine dyes are members of another class of dyes that are selectively retained by tumor cells and certain viruses. For example, Merocyanine 540, (commonly referred to as MC 540) has been used for light-induced tumor and viral chemotherapy. K. S. Gulliya, J. L. Matthews, J. W. Fay, and R. M. Dowben, Proc. SPIE-Intl. Soc. Opt. Engineering 84f7: 163-65 (1987); K. S. Gulliya, S. Pervaiz, D. G. Nealon, and D. v. Vander-Meulen, Proc. SPIE-Intl. Soc. Opt. Engineering 907: 34-36 (1988); F. Sieber, Photochem. and Photobiol. 46: 1035-42 (1987).

The emphasis on using a photoactive compound or dye as the photoactivating or light-activating compound in photoradiation of tumors or viruses is based on two important properties of the photoactive compound or dye. Firstly, the photoactive compound or dye is preferentially accumulated and retained to a higher degree in or around the target tumor or virus than in the surrounding normal body tissues. Secondly, after being retained in or around the tumor or virus, the photoactive compound or dye is properly photoactivated causing the destruction of tumor cells or virus with which the dye has associated. The destruction of tumor cells or virus occurs when they are simultaneously exposed to the dye and light of a suitable wavelength. The generally accepted mechanism of cell kill by photoactivated dye is that when activated by appropriate light, the dye undergoes an energy transfer process with oxygen to form a reactive singlet oxygen, which subsequently oxidizes and kills the cell or virus to which the dye has attached or associated as a substrate. K. R. Weishaupt, C. J. Gomer, and T. J. Dougherty, Cancer Res. 36: 2326-29 (1976); F. Sieber, Photochem. and Photobiol. 46: 1035-42 (1987).

The life-time of the extremely reactive singlet oxygen is extremely short, less than a fraction of microsecond. Hence, the currently accepted method of practicing PDT is to first let the photoactive compound bind to the target tumor cells or viruses, and then activate the bound photoactive compound. Thus, when the reactive singlet oxygen is generated from photoactivation, the target tumor cells or viruses that are in the close proximity to the activated dye and oxygen are destroyed. The normal cells do not preferentially accumulate the photoactive compound, hence generally very little reactive singlet oxygen is generated in their close proximity. Accordingly, the normal cells are generally spared from destruction by the photoactivated photoactive compound. T. J. Dougherty, et at., Photoradiation Therapy: Clinical and Drug Advances. In *Porphyrin Photosensitization*, D. Kessel and T. J. Dougherty, Eds. Plenum Press, N.Y., pp. 3-13, 1983.

It has been reported that dye such as MC 540 will undergo considerable photobleaching when being irradiated with a light source with the wavelength from about 320 to 600 nm. After about 70 minutes, the dye was decomposed as a result of direct oxidation and/or reaction with lipid peroxides. B. Kalyanaraman, J. B. Feix, F. Sieber, J. P. Thomas, and A. W. Girotti, Proc. Natl. Acad. Sci., U.S.A. 84: 2999-3003 (1987). Similarly, irradiation of an aqueous solution of MC 540 with white light fitted with a 360-nm cutoff filter results in a colorless solution in about 20 min. N. S. Dixit and R. A. Mackay, J. Am. Chem. Soc. 105: 2928-29 (1983). Other cyanine dyes also undergo photobleaching in solution. O. Valdes-Aguilera, L. Cincotta, J. Foley, and I. E. Kochevar, Photochem. Photobiol. 45: 337-44 (1987). Consequently, samples of dye solution are always prepared freshly and in the dark.

As can be seen from the discussion above, PDT has one major limitation in practical utility, that is, in order to eradicate from the animal body the tumor cells or viruses on which the photoactive compound or dye resides, such cells or virus must be exposed to an appropriate light source. Thus, to achieve the desired killing, one must find, if at all possible, the target tumor cells which have preferentially accumulated the photoactive compound, and then one must irradiate these target cells inside the animal body with a light source directly. If the tumor, such as solid tumor, is large enough and localized that it can been seen by naked eyes, then the dye can be injected into the tumor itself. There is still the problem of introducing light into the inner portions of the tumor. Moreover, during metastasis, the tumor cells or viruses have spread to other parts of the body and are no longer localized. The dilemma after the introduction of photoactive compound to the patient is: Where should the irradiation be given? Even assuming that the malignant tumor cells can be localized and found in one particular body tissue or organ, many body tissues and internal organs where tumor cells or viruses have proliferated are nonetheless inaccessible to any light.

Another major limitation to PDT is that the light energy itself, in particular the ultraviolet light, is toxic and can be mutagenic to normal cells as well normal tissues. Thus, many photoactive compounds that can be activated best by ultraviolet light cannot be used in the clinic because the ultraviolet light required for the activation of the compounds would be exceedingly harmful to the surrounding normal tissues and the normal cells.

SUMMARY OF THE INVENTION

According to the present invention, new pre-activated therapeutic agents are provided. The new therapeutic agents comprise a photoactive compound dissolved in a pharmaceutically acceptable carrier producing a solution to which is introduced a sufficient amount of activating agent, prior to being brought into contact with the tissue to be treated, such that the photoactive compound is activated to produce a therapeutic mixture. The photoactive compound used is characterized in that it contains at least one chromophore and that it is susceptible to activation by an activating agent.

The therapeutic mixture of the invention is characterized in that subsequent to activation, it is still capable of interacting with and destroying or destructing tumors or other pathogenic biological contaminants infecting body tissues; and that subsequent to activation, it is, at effective dosages, relatively non-toxic to normal tissues or normal cells, and that its therapeutic properties are retained for at least about 10 seconds at ambient temperature subsequent to activation.

The present invention also provides an efficient and economical method for the preparation of pre-activated therapeutic agents for the destruction of malignant tumor cells or other pathogenic biological contaminants infecting body tissues either in the animal body or outside the animal body. Broadly, the method comprises the steps of dissolving a photoactive compound in a pharmaceutically acceptable carrier to produce a resultant solution and then, prior to being brought into contact with tissues to be treated, introducing a sufficient amount of activating agent to the resultant solution such that the photoactive compound is activated and subsequently capable of interacting with, and destructing or destroying, tumors or other pathogenic biological contaminants infecting the body tissues.

The present invention further provides a method of treating body tissues, which are infected with tumors or other pathogenic biological contaminants, either inside the animal body, such as human body, or outside the animal body. The method comprises the steps of first activating a photoactive compound dissolved in a pharmaceutically acceptable carrier to produce a therapeutic mixture and then administering the therapeutic mixture containing an effective amount of the activated compound to such body tissues, which are infected with tumors or other pathogenic biological contaminants having an affinity to the activated photoactivated compounds. The method of treatment can be carried out either inside the animal body, such as human body, or outside the animal body.

Accordingly, an object of the invention is to provide therapeutic agents which have been pre-activated and which are subsequently capable of interacting with and destructing or destroying tumors or other pathogenic biological contaminants infecting body tissues of an animal.

Another object of the invention is to provide therapeutic agents which have been pre-activated and which are capable of interacting with and destructing or destroying tumors or other pathogenic biological contaminants infecting body tissues of an animal, such that no further activation with a possibly harmful activating agent or magent is required.

Yet another object of the invention is to provide a method for activating a photoactive compound before introducing the compound into the body of an animal, such as human, thus eliminating the necessity of post-activating the compound at the target site after it has entered the body.

Another object of the invention is to provide a method for the treatment of an animal, such as human, infected with malignant tumors or other pathogenic biological contaminants having an affinity to the activated photoactive compound or dye.

Still another object of the invention is to provide a method for the treatment of body tissues outside the body of an animal, such as human, infected with malignant tumors or other pathogenic biological contaminants having an affinity to the activated photoactive compound or dye.

A still further object of the invention is to provide pre-activated therapeutic agents which rapidly clear normal cells or normal body tissues but not rapidly clear tumor tissues or other pathogenic biological contaminants.

A still further object of the invention is to provide pre-activated therapeutic agents which are selective toward tumor cells or other pathogenic biological contaminants.

A still further object of the invention is to provide a method of producing the above-identified pre-activated therapeutic agents.

A still further object of the invention is to provide a method of pre-activating the above-identified therapeutic agents with radiation energy, electromagnetic energy, electrical energy, or chemicals.

A yet further object of the invention is to provide a method and therapeutic agents for selectively adhering to or associated with cells for photodynamic, chemical, or electrical action in conjunction with other agents.

In accordance with the above noted and other objects of the invention, pre-activated therapeutic agents are obtained from photoactive compounds or dyes. These pre-activated therapeutic agents have a preference for the undesirable cells or pathogenic biological contaminants. Generally, these pre-activated therapeutic agents or mixtures comprise activated photoactive compounds dissolved in a pharmaceutically acceptable carrier. These pre-activated therapeutic agents have the following desirable properties: (1) Subsquent to pre-activation outside the body or body tissue, they still retain, in the animal body or body tissue, their preferential affinity, hence preferential toxicity, toward tumors or other pathogenic biological contaminants infecting the animal body or body tissue; (2) after they have been pre-activated, there is no need to further activate them by the activating agent inside the animal body or body tissue; (3) they are stable and retain their biological and therapeutic activities for at least 10 seconds at room temperature, and some can be kept for days if kept in the dark and under low temperature; (4) they can be pre-activated by radiation energy, electromagnetic energy, electrical energy, electrons, or chemicals; (5) they are preferentially associated with tumor cells or other pathogenic biological contaminants over normal body tissues; (6) they are efficient in destructing or destroying the tumor cells or other pathogenic biological contaminants with which they have associated; (7) in effective doses, they are relatively non-toxic against normal cells or normal body tissues; (8) they can be combined with certain other agents to achieve a greater percentage kill of the tumor cells or other pathogenic biological contaminants infecting an animal, such as human, or a body tissue; (9) certain other chemomodifying agents can assert a synergistic therapeutic effect when combined with them; (10) because they are pre-activated away from the target sites and outside the animal body and because, once pre-activated, they require no further activation in the animal body, they can be pre-activated by activating agent such as ultraviolet radiation which, by itself, is undesirable and mutagenic; and (11) they can prolong the survival time of the tumor-bearing animal as compared to the untreated control animal. Other objects, advantages and features of the present invention will become clear from the following detailed description when read in conjunction with the tables and appended claims.

The fact that photoactive compounds can be activated away from the targets to produce a pre-activated therapeutic agent which retains its therapeutic activities subsequent to the activation is astonishing and totally unexpected. The presently accepted teaching is that to be therapeutically effective, the activation must be accomplished at the target sites. Yet the present invention shows that photoactive compounds can indeed be activated away from, and before being brought into contact with, the target site.

DETAILED DESCRIPTION

The present invention provides a method, composition, and solution for the preparation, as well as its method of application and utilization, of pre-activated therapeutic agents derived from activated photoactive compounds capable of destructing of destroying malignant tumor cells or other pathogenic biological contaminants infecting body tissues either in the animal body or outside the animal body.

The term "pre-activated" as used herein denotes that the photoactive compound is activated, sensitized, or excited outside the animal or human body, or outside the body tissues. Thus, the term "pre-activated" denotes that the activation of the photoactive compound is accomplished away from the body tissue to be treated, away from the target tumor cells or target biological pathogenic contaminants. Hence, the activation step in the "pre-activated" method is carried out before, not after, the photoactive compound has interacted with the target tumor cells or with other pathogenic biological contaminants. In fact, the activation step in the "pre-activated" method is carried out prior to the photoactive compound has been brought into contact with the tissue to be treated. There is no requirement for further activation at the target sites once the therapeutic agent has been pre-activated. The pre-activated therapeutic agent so generated has a measurable and clinically useful shelf life time.

The activating agent as used herein denotes a means or an agent that is capable of activating, exciting, or sensitizing a photoactive compound. The activating agent can be radiation energy, the entire spectrum of electromagnetic energy, laser, heat energy, electric current, electrons, or chemicals. The electromagnetic spectrum can be the entire range of wavelengths or frequencies of electromagnetic radiation extending from gamma rays to the longest radio waves and including visible light, xenon light, laser light, and ultraviolet light. The laser or other radiation energy can be continuous or pulsed. The pulsed energy used is such that the energy supplied has a multiple number of short pulses of relatively high energy, but at the same time, has a much lower average energy rate. The laser could be gold vapor laser, xenon laser, argon laser, a crystal laser, a gas discharge laser, an excimer laser, krypton laser, argon ion pumped dye laser, or hollow cathode metal vapor laser, and others. Even sources such as conventional filament lamp source with appropriate filtering, an arc lamp source with appropriate filtering, or even a pulsed xenon flash lamp with appropriate filtering could be used.

The term "interact" as used herein denotes the general phenomena of having the therapeutic agent adhering to, accumulate in, or associated with the tumor cells or other pathogenic biological contaminants infecting a body tissue.

The photoactive compounds are generally compounds, such as dyes, having one or more chromophores and capable of absorbing light energy. The term "chromophore" refers to portions of a molecule that are fundamentally responsible for the electronic transition. These photoactive compounds can be cationic, anionic, zwitterionic, or neutral. They comprise chemical classes, and their respective derivatives, including, but are not limited to: acridine; anthraquinone; azine; azo, which comprises disazo, monoazo, pyrazolones, and triazo; azomethine; coumarins; diphenylmethane; flaven; flavone; flavylium salts; indigoid; methylidyne; nitro; nitroso; polymethylidyne; natural dyes such as porphyrin derivatives; psoralens; quinonimines; sulfide; sulfur; thiazole; toluidine; triphenylmethane; xanthene; and others.

The term "pathogenic biological contaminants" is to be understood to include: viruses, enveloped or not enveloped; microorganisms; parasites; bacteria and the like.

"Tumors" or "tumor cells" is understood to include, among others: cancer of the bone and connective tissues; cancer of the eyes; leukemias; lymphomas; myelomas; melanomas, breast cancer, lung cancer, ovarian cancer as well as other types of cancer and solid tumors.

The term "body tissue" as used herein is to be understood to include "body fluid," red blood cells, white blood cells, platelets, cryo precipitate from blood plasma, other plasma proteins, bone marrow, skin, cornea, and other tissues from an animal or a human.

The term "body fluid" as used herein is to be understood to include whole blood, any formed elements of the blood, blood plasma, serum, fluids containing such components, fluids from plasmapheresis, plasma fibrinogen, cryo-poor plasma, albumin, gamma globulins, semen, and other fluids introduced or intravenously injected into the body of a patient or an animal using known administration techniques. The term "body fluid" is to be understood to include body fluid prior to, or after, physical as well as chemical fractionation, separation or freezing.

The term "external" as used herein is to denote outside the animal or human body.

The term "animal" as used herein is to denote any warmblooded animal; this includes human and other domestic and farm animal.

The term "carrier" as used herein denotes a vehicle, a solution containing water, buffers, serum, serum proteins, lipoproteins, artificial bio-membranes, liposomes, monoclonal antibodies, carbohydrates, cyclodextrans, organic solvents or other pharmaceutically acceptable, or compatible, solutions. The carrier, or vehicle, is to dissolve any of the above-described photoactive compound and to enhance its delivery into effective proximity to the target tumor cells or other pathogenic biological contaminants infecting body tissues. The final carrier, or vehicle, used is pharmaceutically compatible in that it is relatively non-toxic to the normal cells and normal tissues and it does not react with the solute or therapeutic agent contained therein.

. The phrase "chemomodifying agent" as used herein is to denote an agent, such as a chemical or any other agent, that can potentiate, augment or increase the therapeutic efficacy of a therapeutic agent. Hence, a chemomodifying agent can synergize the therapeutic efficacy of a therapeutic agent.

The phrase "effective dosage" as used herein is to denote the concentration or level of the therapeutic agent that can attain a particular medical end, such as a cure or a destruction of the undesirable cells, such as tumor cells, or pathogenic biological contaminants, without producing a pronounced toxic symptoms.

The present invention provides pre-activated therapeutic agents, a method for its preparation, and methods of its application to treat tissues, either externally or inside the body, infected with tumor or other pathogenic biological contaminants.

The pre-activated therapeutic agents comprise a photoactive compound dissolved in a pharmaceutically acceptable carrier to produce a resultant solution. To this resultant solution is introduced a sufficient amount of activating agent such that the photoactive compound is activated to produce a therapeutic mixture. The therapeutic mixture is characterized in that subsequent to activation, it is still capable of interacting with and destructing or destroying tumors or other pathogenic biological contaminants infecting body tissues, and that subsequent to activation, it is, at effective dosages, relatively non-toxic to normal tissues or normal cells. Further, its therapeutic properties are retained, in whole or in part, for at least about 10 seconds at ambient temperature subsequent to activation. The two phrases "therapeutic mixture" and "therapeutic agent" as used herein are interchangeable in that the step of activating a photoactive compound with an activating agent may yield a single agent or a mixture, all or one or more than one component in any combination of which are biologically or therapeutically active.

Photoactive compounds which are selective for tumor or other pathogenic biological contaminants, and which can be used in the eradication or destruction of such tumor cells or contaminants in accordance with the present invention, must satisfy the following criteria:

(1) These photoactive compound must have one or more chromophores. Portions of their molecules must be fundamentally responsible for the electronic transition. They are capable of absorbing light energy;

(2) These photoactive compounds must be capable of being activated or sensitized by an activating agent, such as radiation energy, electromagnetic energy, electrical energy, electrons, or chemical;

(3) After they have been activated by an activating agent outside the body or body tissue, the resultant therapeutic mixture or agent must still retain, in the animal body or body tissue, its preferential affinity, hence preferential toxicity, toward tumors or other pathogenic biological contaminants infecting the animal body or body tissue;

(4) After they have been activated by an activating agent outside the body or body tissue, the resultant mixture or agent does not require further activation by the activating agent inside the animal body or body tissue;

(5) After they have been activated by an activating agent outside the body or body tissue, the resultant therapeutic mixture or agent must be relatively and that it must retain its biological or therapeutic activities for at least 10 seconds at room temperature, and some for days if kept in the dark and under low temperature;

(6) After they have been activated by an activating agent outside the body or body tissue, the resultant therapeutic mixture or agent is preferentially associated with tumor cells or other pathogenic biological contaminants over normal body tissues or normal cells;

(7) After they have been activated by an activating agent outside the body or body tissue, the resultant therapeutic mixture or agent is efficient in destructing or destroying the tumor cells or other pathogenic biological contaminants with which it has associated;

(8) After they have been activated by an activating agent outside the body or body tissue, the resultant therapeutic mixture or agent, in effective doses, is relatively non-toxic against normal cells or normal body tissues;

(9) After they have been activated by an activating agent outside the body or body tissue, the resultant therapeutic mixture or agent can be combined with certain other agents to achieve a greater percentage kill of the tumor cells or other pathogenic biological contaminants infecting an animal, such as human, or a body tissue; and

(10) After they have been activated by an activating agent outside the body or body tissue, the resultant therapeutic mixture or agent can be combined with certain other chemomodifying agents, such as a chemical, electrons, electrical current, or gamma rays, to augment or enhance the therapeutic effect of the resultant therapeutic mixture.

Generally, a stock solution of the pre-activated therapeutic agent or mixture is prepared by dissolving an appropriate concentration of photoactive compound in an appropriate pharmaceutically acceptable carrier or vehicle as defined above. The resultant solution is then subjected to a sufficient amount of activating agent to produce a therapeutic agent or mixture such that the photoactive compound dissolved therein is activated and subsequently, in the absence of the activating agent, capable of interacting with, and destroying, tumors or other pathogenic biological contaminants infecting the body tissues. Aliquots of the stock solution are then removed and diluted with appropriate pharmaceutically acceptable carrier or vehicle to the desired concentrations. Depending on the photoactive compound used, the stability of the resultant therapeutic agent or mixture can vary. Nevertheless, it is stable at room temperature for at least a few minutes to be clinically and practically useful. Some of the pre-activated therapeutic agent or mixture is even stable for days if kept in the dark and at low temperature. The term "stability" as used herein denotes the ability for the pre-activated therapeutic agent or mixture to exert its biological or therapeutic properties after storage.

Pre-activated therapeutic solutions with the desired concentration can then be used for either the in vitro or the in vivo application. In the in vitro application, solution containing the appropriate concentration of the pre-activated therapeutic agent or mixture is administered into body tissue or cells outside the animal body, such as human body. The mixture containing the pre-activated therapeutic agent and the tissues or cells to be treated is then incubated at an appropriate temperature for a desired duration of time. This application is useful, for example, for the extracorporeal treatment of body tissues, such as human tissues, to eradicate tumor cells or other pathogenic biological contaminants infecting such body tissues. In the in vivo application, the solution containing the appropriate concentration of pre-activated therapeutic agent or mixture is directly administered into the animal body. This application is useful, for example, for the treatment of animal, such as human, infected with tumor or other pathogenic biological contaminants.

Some of the preferred activating agent include, but are not limited to: radiation in the entire absorption spectrum or region of the photoactive compound, preferably around the relatively strong or near maximum absorption regions of the molecules; gamma rays; electrons generated by an electropotential device; and chemical.

Any suitable source can be employed to irradiate the photoactive compound, provided such source produces sufficient radiation to activate the photoactive compound and to provide the resultant therapeutic agent or mixture with the desired properties mentioned above. The operable source employed to irradiate the resulting fluid has a wavelength of from about 230 nm to about 1200 nm and an energy density of from about 0.1 J/cm$^2$ to about 3000 J/cm$^2$. Suitable light sources include, but are not limited to, sources that generate a specific wavelength range of radiation and sources that are fitted with appropriate filter to reduce the undesirable ranges of wavelengths.

Because the pre-activation of the therapeutic agent, or the activation of the photoactive compound, takes place before, not after nor during, the agent or compound is brought into contact with tissues, extracorporeally or outside the body, the activating agent used can even be a potentially lethal or dangerous radiation, such as UV or gamma rays. The UV or gamma rays used to activate the photoactive compound will not be in contact with any body tissue. Hence, they will not harm the body tissues or the host, such as the human subject or patient.

Flow of electrons or electric current, such as that generated by two electrodes, can also be used to activate the photoactive compound. The electrodes are made of a cathode and an anode. They can be powered by any conventional power source, such as a direct current battery or others. The operable voltage or current has a low amperage but high voltage, such as from about 100 volts to about 5000 volts in a range of milliamps.

Certain chemicals, such as chloroquine, hydrogen peroxide, certain reducing agents or certain oxidizing agents can also be used to activate the photoactive compund.

Certain chemomodifying agents, such as buthionine sulfoximine (BSO; commercially available from Sigma, St. Louis, Mo. can be used to potentiate or augment the therapeutic efficacy or activity of the pre-activated therapeutic agent or mixture. BSO is a compound which depletes cells of cellular glutathione (GSH) by inhibiting the synthesis of GSH, yet it has been shown in in vivo screenings to be relatively non-toxic. M. J. Allalunis-Turner, F. Y. F. Lee, and D. W. Siemann, Cancer Res. 48: 3657-60 (1988); F. Y. F. Lee, D. W. Siemann, M. J. Allalunis-Turner, and P. C. Keng, Cancer Res. 48: 3661-65 (1988).

As previously set forth, the present invention provides an effective pre-activated therapeutic agent, and methods of its preparation as well as its practical application and utility, for the destruction, killing, or eradication of tumor cells and other pathogenic biological contaminants infecting the body tissues, either inside the animal body or outside the animal body. Such animal can be a human. The contaminants that can be eradicated include the enveloped viruses, non-enveloped viruses, and other microorganisms, including other parasites and bacteria.

The term "enveloped virus" in all cases but one is understood to be a virus of which is encased within a modified host cell membrane, except for the Pox-virus which produce their own envelope. Among families of enveloped viruses are: Herpesviridae; Iridoviridae; Poxviridae; Hepadnaviridae; Orthomyxoviridae; Paramyxoviridae; Rhabdoviridae; Bunyaviridae; Filoviridae; Nodaviridae; Togaviridae; Flaviviridae; Retroviridae; and Arenaviridae. Among common species or genus of such enveloped viruses are: Cytomegalovirus; *herpes simplex* virus; Pox virus; human immunodeficiency virus; Epstein-Barr virus; and others.

Among families of "non-enveloped" viruses are: Parvoviridae; Papovaviridae; Adenoviridae; Picornaviridae; Caliciviridae; Reoviridae; and Coronaviridae. Among common species or genus of such non-enveloped viruses are: parvovirus; papillomavirus; adenoviruses; polioviruses; and others.

Among the parasites are: Parasitic Protozoa; Kinetoplastida; Sarcodina; Apicomplexa; Phyla Myxozoa Microspora; Platyhelminthes; Trubellaria; Trematoda; Digenea; Anepitheliocystidia; Cestoidea; Nematoda; Trichurata Dioctophymata; Oxyurata; and Spirurata. Also included are malaria, trypanosoma, schistosoma, teniasolium, teniasaginata, acanthamaoeba, and echinococcus.

Included in the bacteria are gram-positive and gram-negative bacteria.

Other microorganism which can be effectively eradicated by the method of the present invention include, but are not limited to: *Plasmodium vivax, P. malariae, P. falciparum, P. ovale, Trypanosoma cruzi, Bacillus subtilis,* and *Streptococcus faecalis.*

Merocyanine 540 (MC 540; 1,3 dibutyl-5-[4-[3-(3-sulfopropyl)-2-benzoxazolinylidine]-2,4-butenylidene]-2-thiobarbituric acid sodium salt) (commercially available either from Sigma Chemical Co. in St. Louis, MO., or from Eastman Kodak in Rochester, N.Y.) was typically activated by dissolving 1 milligram of this photoactive compound in 1 ml of 1:1 ratio of 95% ethanol and water, although smaller amount of the ethanol (about 15% in volume) had been successfully used for the preparation of the therapeutic mixture used for injecting into the animal body, the in vivo studies. The resultant solution was placed in a 35×10 mm Falcon petri dish and then irradiated with a laser light at 514 nm maintained at 2.5 watts for 45 minutes. The light source used was an argon ion laser (Spectra Physics Model 171) with a model 270 power supply. In some experiments, relatively broad range of wavelength of light (from about 400 nm to 560 nm) was also used successfully. During the irradiation, the petri dish was kept on a ¼ inch thick plate that acted as a heat sink. Irradiation by laser light was carried out at room temperature. In some experiments, the solution was gently agitated during the irradiation. Final dilution were made in plain RPMI 1641 medium (GIBCO, Grand Island, N.Y.) to obtain the desired concentrations. The pre-activated therapeutic agent so prepared was used in both in vivo and in vitro experiments unless otherwise stated.

Dihematoporphyrin ether (DHE) (sometimes known as Photofrin II; commercially available from Quadra Logic Technologies, Inc., Vancouver, British columbia, Canada) was similarly activated. The photoactive DHE (obtained in solution) was mixed with either saline solution or RPMI-1640 complete medium to obtain the desired concentrations and irradiated with laser light for about 40 minutes in the wavelength range of from about 600 nm to about 650 nm maintained at about 150 m watts.

Methylene Blue (commercially available from Eastman Kodak, Rochester, N.Y.) either in saline solution or in RPMI-1640 complete medium was irradiated with laser light for about 20 minutes in the wavelength range of from about 600 nm to about 650 nm maintained at about 200 m watts.

Benzoporphyrin derivatives were synthesized from protoporphyrin and involving the formation of Diels-Alder adducts. Briefly, protoporphyrin IX dimethyl ester (500 mg, 0.85 mmol) was dissolved in dry toluene (50 ml), and diethyl acetylenedicarboxylate (0.5 ml, 3.15 mmol) was added. The reaction mixture was refluxed in the dark for 6 days. The solvent was removed in vacuo, and the residue was purified by chromatography on silica gel with dichloromethane/2% diethyl ether. After limited hydrolysis with 25% HCl, the reaction yielded four components, mono- and di-acid derivatives of either ring A or ring B fused porphyrins (MAA, MAB, DAA, and DAB, respectively). The methods of synthesis, such as those disclosed by J. S. Pangka, A. R. Morgan and D. Dolphin, J. Org. Chem. 51: 1094-1100 (1986), were employed, and the disclosure of which is incorporated by reference herein. The four isomers, namely, MAA, MAB, DAA, and DAB, were activated as above. Each compound was dissolved in a complete medium (a medium where all necessary growth constituents for the growth or maintenance of cells of a given type have been added) and irradiated for about 20 minutes with a laser light at a wavelength range of from about 650 nm to about 720 nm maintained at 150 m watts.

N,N'-Bis(2-ethyl-1,3-dioxolane)kryptocyanine (EDKC) can be prepared by methods such as those disclosed by F. M. Hammer, J. Chem. Soc., 2796-2804 (1927), and the disclosure of which is incorporated by reference herein. In brief, 1-(2-ethylene-1,3-dioxolane)-4-methylquinolinium bromide (0.66 g, 2 mmol) and dry pyridine (6 ml) are stirred at 110° C. under a nitrogen atmosphere until solution occurred. To this is to be added triethylorthoformate (0.75 g, 5 mmol) and stirring is to continue for 2 hr. The deep cyan colored solution is to be cooled and poured into rapidly stirred ethyl ether (200 ml). The crude product can be isolated by filtration and purified by medium-pressure column chromatography (Woelm 32-63 silica gel, methylene chloride/methanol). The fractions that are homogeneous by thin layer chromatography analysis (silica gel, 5% methanol/methylene chloride) are to be combined. A solution of the resultant EDKC in a complete medium can be irradiated with laser light for about 10 minutes around the wavelength region from about 650 nm to about 725 nm maintained at about 1 to 2 watts.

Pre-activated therapeutic agent prepared from or derived from MC 540 activated by laser light is a powerful anti-tumor agent particularly against the leukemias and lymphomas. The activity of the compound in vivo against L1210 leukemia transplanted into mice is demonstrated in the following experimental study.

Female DBA/2 NIT mice, 6-8 weeks old, were obtained from Charles River, Wilmington, MA. These mice, weighing about 25 g. each, were each inoculated intraperitoneally (i.p.) on Day "0" with about $4 \times 10^6$ cells of the murine leukemia, L1210. Six days later (Day 6), each mice was again inoculated intraperitoneally with $3 \times 10^6$ of similar L1210 leukemia cells. One day later (Day 7), the mice were treated i.p. with pre-activated therapeutic agent derived from MC 540 at a level of 3.2 mg/kg in a volume of 200 µl per mouse. The treatment with pre-actived therapeutic agent derived from MC 540 was repeated, at similar dosages, on Days 10 and 12. On Days 13, 14 and 16, each of the treated mice was injected i.p. with pre-activated therapeutic agent derived from MC 540 at a dosage of 20 mg/kg. Thus, within a span of 16 days, each of the treated mice received a total of 109.6 mg/kg of the pre-activated therapeutic agent derived from MC 540.

Injections of similar mixture of ethanol and water were used as controls. The control L1210-bearing mice died on Day 14, on the average.

The L1210-bearing mice treated with pre-activated therapeutic agent derived from MC 540 discussed above lived to Day 24, on the average. Thus, the treated mice showed an extension of life-span of about 71%.

Experiments were also carried out to establish the relatively non-toxic nature of pre-activated therapeutic agents derived from photoactive compounds toward normal human cells. Experiments were likewise carried out to determine the inhibition of growth of various tumor cells in the presence of pre-activated therapeutic agents or mixtures derived from photoactive compounds in culture, the in vitro experiments. Moreover, experiments were performed to demonstrate the antiviral and anti-parasitic properties of the pre-activated therapeutic agent or mixture derived from photoactive compounds. The following examples describe the method and manner of carrying out the experiments but are not to be construed as limiting.

All cell lines for the following examples were obtained from the American Type Culture Collection (ATCC, Rockville, MD.) and maintained in recommended growth medium at 37° C. in a humidified 5% $CO_2$ incubator. The acute promyelocytic leukemia cell line HL-60 was maintained in RPMI-1640 supplemented with 10% fetal bovine serum (FBS), 100 units penicillin/100 µg streptomycin, and 0.25 mM L-glutamine (Gibco, Grand Island, N.Y.) at 37° C. in a humidified atmosphere of 5% $CO_2$ in air. Cells were maintained in log phase with more than 95% viability. H-69, HS-Sultan and ARH-77 cell lines were maintained in IMDM (Iscoves Modified Dulbecco's Medium) and 10% FBS. BT-20 cell line was maintained in Eagle's minimum essential medium with Earle's salts with nonessential animo acids plus 10% FBS. MCF-7 cell line was maintained as above but sodium pyruvate was added. Other cell lines were maintained in RPMI-1640 medium in the presence of 10% FBS.

The general method of maintaining different cell lines has been described in publications by Gulliya, et. al., and are hereby incorporated by reference. K. S. Gulliya, J. L. Matthews, J. W. Fay, and R. M. Dowben, Life Sci. 42:2651-56 (1988); K. S. Gulliya, S. Pervaiz, D. G. Nealon, and D. F. Vander Meulen, Proc. SPIE 907: 34-36 (1988); K. S. Gulliya, J. L. Matthews, j. W. Fay, R. M. Dowben, Proc. SPIE 847: 163-165 (1987).

Normal bone marrow cells were obtained from patients in marrow transplantation research protocols. Methods of maintaining bone marrow cell cultures, such as those disclosed by K. S. Gulliya, et. al., Life Sci. 42: 2651-56 (1988), were employed, and the disclosure of which is incorporated by reference herein.

Normal cells and tumor cells were treated with different freshly prepared pre-activated therapeutic agents or mixtures derived from photoactive compounds at different final concentrations. To study the effect of each pre-activated therapeutic agent derived from a photoactive compound, the treated cells were incubated at 37° C. for 24 hours in the presence of the pre-activated therapeutic agent derived or prepared from the photoactive compound. The viability of cells in certain experiments was determined by Trypan Blue dye exclusion method. In another set of experiments, cell were treated with pre-activated therapeutic agents derived or prepared from photoactive compounds for 24 hours at 37° C. At the end of the incubation period, radioactive alanine or thymidine was added to the cell suspension. After another 24 hour incubation period at 37° C., the cells were harvested by PHD-cell harvester and the radioactive incorporation was determined by a Beckman LS1701 liquid scintillation counter. Inhibition of DNA or protein synthesis as determined by $^3$H-thymidine or $^3$H-alanine incorporation was interchangeably used with percent cell viability. In most experiments, the viability of cells was also determined by Trypan Blue dye exclusion method in addition to the determination based on DNA or protein synthesis.

Methods of in vitro assay, such as those disclosed in Selected Methods in Cellular Immunology, Eds. B. B. Mishell and Stanley M. Shiigi, W. H. Freeman and Company, San Francisco, CA, 1980, were employed, and the disclosure of which is incorporated by reference herein.

EXAMPLE I

Fresh normal peripheral blood lymphocytes from normal human blood were treated with pre-activated therapeutic agent derived from MC 540 for 24 hours at 37° C. After this incubation period, cells were stimulated by 100 µg/ml of phytohemagglutinin (PHA) for 42 hours and $^3$H-thymidine (4 µCi/ml) was added for the last 24 hours. After 72 hours of incubation, cells were harvested by PHD-cell harvestor and $^3$H-thymidine incorporation was determined as counts per minute (CPM) and compared to the control to determine the percent viability.

Tumor cells were treated with pre-activated therapeutic agent derived from MC 540 for 24 hours at 37° C. After the incubation period, $^3$H-thymidine was added and incubated for another 24 hours. After a total of 48 hours, tumor cells were harvested as described above, except that these cells were not stimulated with PHA.

The data presented in Table 1 show that pre-activated therapeutic agent derived or prepared from MC 540 activated by laser light was relatively non-toxic to normal human peripheral blood lymphocytes originated from normal human blood. In contrast, human leukemia cells, human Burkitt lymphoma cells, human cutaneous T-cell lymphoma cells, human histiocytic lymphoma cells, human small cell lung carcinoma cells and murine leukemia cells were all susceptible to destruction by the pre-activated therapeutic agent derived from MC 540. This pre-activated therapeutic agent killed over 90% of these tumor cells. Under similar conditions, multiple myeloma cells were, however, less sensitive to pre-activated therapeutic agent derived from MC 540 activated by laser light.

TABLE 1

EFFECT OF PRE-ACTIVATED THERAPEUTIC AGENT DERIVED FROM PHOTOACTIVE COMPOUND MEROCYANINE 540 (MC 540) ON NORMAL AND TUMOR CELLS

| Cell Type | Origin of Cells | Percent Viability Of Cells After Treatment |
|---|---|---|
| Peripheral Blood Lymphocytes | Normal Human Blood | 85** |
| Peripheral Blood Lymphocytes | Normal Human Blood | 90* |
| HL-60 | Human Leukemia | 2.6 |
| Daudi | Human Burkitt Lymphoma | 4.6 |
| L1210 | Murine Leukemia | 2.4 |
| HS-Sultan | Human Multiple Myeloma | 79 |
| ARH-77 | Human Multiple Myeloma | 100 |
| GM-1312 | Human Multiple Myeloma | 25 |
| HUT-78 | Human Cutaneous T-Cell Lymphoma | 2.5 |
| U-937 | Human Histiogtic Lymphoma | 5.6 |
| H-69 | Human Small Cell Lung Carcinoma | 9.0 |

A final concentration of 40 µg/ml of the pre-activated therapeutic agent derived from MC 540 was used for this set of experiments. Viability was determined from the $^3$H-thymidine incorporation.
*Viability of the cells was determined by Trypan Blue dye exclusion method. Treatment was carried out in the presence of 10% FBS.
**Treatment was carried out in the presence of 10% FBS.

EXAMPLE II

Results presented in Table 2 show that, similar to pre-activated therapeutic agent derived from MC 540, pre-activated therapeutic agent derived from dihematoporphyrin ether (DHE) activated by laser light was also relatively non-toxic toward normal peripheral blood lymphocytes originated from normal human blood. In contrast, human leukemia cells and human Burkitt lymphoma cells were highly sensitive to, and hence were killed, or destroyed, by, pre-activated therapeutic agent derived from DHE.

From the above Table, it is apparent that the invention has produced a near total destruction of a number of tumor cells without adverse effects on normal cells.

TABLE 2

EFFECT OF PRE-ACTIVATED THERAPEUTIC AGENT DERIVED FROM PHOTOACTIVE COMPOUND DIHEMATOPORPHYRIN ETHER (DHE) ON HUMAN NORMAL AND TUMOR CELLS

| Cell Type | Origin of Cells | Percent Viability Of Cells After Treatment |
|---|---|---|
| Peripheral Blood Lymphocytes | Normal Human Blood | 85 |
| HL-60 | Human Leukemia | 8 |
| Daudi | Human Burkitt Lymphoma | 10.0 |

A final concentration of 12.5 µg/ml of pre-activated therapeutic agent derived from DHE was used for this set of experiments. Viability was determined from the $^3$H-thymidine incorporation.

EXAMPLE III

A stock solution of MC 540 was prepared by dissolving the photoactive compound MC 540 in a mixture of 1:1 95% ethanol and water. The desired amount of MC 540 solution was then either mixed with RPMI-1640 medium (with or without serum) or placed as was in a sterile petri dish (35 × 10 mm). The petri dish containing the solution of MC 540 was then irradiated with 514 nm laser light for different amounts of time as discussed above. The resultant pre-activated therapeutic agent was then used to determine its tumor-cell killing efficacy. It is seen from data presented in Table 3 that the duration of activating the photoactive compound MC 540 affected the therapeutic efficacy of the pre-activated therapeutic mixture so prepared. For most applications, 8 minutes of laser irradiation at 2 watts was sufficient to activate 20 µg/ml of MC 540.

TABLE 3

EFFECT OF THE DURATION OF ACTIVATION BY RADIATION OF MEROCYANINE 540 ON ITS SUBSEQUENT CYTOTOXICITY TOWARD TUMOR CELLS*

| Duration Of Irradiation In Minutes | Percent Viability Of Daudi Cells | Percent Viability Of H-69 Cells |
|---|---|---|
| 2 | N.D.** | 30.4 |
| 4 | 20 | N.D.** |
| 8 | 32 | 51.2 |
| 16 | 26 | 46.6 |
| 32 | 0.2 | 63.2 |
| 60 | 0.6 | 41.0 |

*Merocyanine 540 was activated by irradiation with a laser light at 514 nm for different duration of time before being brought into contact with tumor cells. The resultant therapeutic mixture (40 µg/ml) was incubated overnight with tumor cells. Viability of the tumor cells was determined by Trypan Blue dye exclusion method. Daudi cells, originating from human Burkill lymphoma, were maintained in 2% FBS; H-69 cells, originating from human small cell lung carcinoma, were maintained in 10% FBS.
**N.D. = Not determined.

EXAMPLE IV

A stock solution of MC 540 was prepared by dissolving the photoactive compound MC 540 in a 1:1 mixture of 95% ethanol and water. The desired amount of MC 540 solution was then either mixed with RPMI-1640 medium or placed as was in a sterile petri dish (35×10 mm). The petri dish containing the solution of MC 540 (for a final concentration of 20 µg/ml in cell culture) was then irradiated with 514 nm laser light for about 8 minus at 2 watts to yield the pre-activated therapeutic agent. Aliquots of the pre-activated therapeutic agent derived from MC 540 was then stored at different temperatures and for different durations of time. After the storage, the remaining therapeutic activity of the pre-activated therapeutic agent was determined by its ability to kill Daudi tumor cells as compared to that of a freshly prepared sample. Data presented in Table 4 show that after storing at 4° C. for 1 day, the pre-activated therapeutic agent derived from MC 540 retained its therapeutic activity that was about 60% of that of the freshly prepared sample. After 15 days at −10° C., the pre-activated therapeutic agent derived from MC 540 irradiated with laser light retained about half of its therapeutic activity as compared to a freshly prepared sample. After 7 days at −75° C., the pre-activated therapeutic agent derived from MC 540 still retained about 96% of its original therapeutic activity. After 7 days at −135° C., none of its therapeutic activity was lost as compared to the freshly prepared sample. Thus, the lower the temperature at which the pre-activated therapeutic agent was stored, the longer it would retain its tumor-killing ability. It is clear that the present invention provides a pre-activated therapeutic agent that is stable and that retains its ability, in whole or in part, to kill tumor cells for quite some time after the activating agent, in this case the laser light, was removed.

TABLE 4

EFFECT OF THE STORAGE TEMPERATURE AND TIME ON THE RETENTION OF THE THERAPEUTIC ACTIVITIES OF PRE-ACTIVATED THERAPEUTIC AGENT DERIVED FROM PHOTOACTIVE COMPOUND MEROCYANINE 540 (MC 540)

| Storage Temperature In °C. | Number Of Days Stored | Percentage Of Remaining Therapeutic Activities* |
|---|---|---|
| Freshly Prepared | 0 | 99 |
| 4 | 1 | 60 |
| −10 | 1 | 90 |
|  | 2 | 90 |
|  | 7 | 90 |
|  | 15 | 50 |
|  | 30 | 0 |
| −75 | 1 | 96 |
|  | 2 | 96 |
|  | 7 | 96 |
|  | 15 | 80 |
| −135 | 1 | 99 |
|  | 2 | 99 |
|  | 7 | 99 |
|  | 15 | 75 |
|  | 30 | 60 |

*Remaining therapeutic activities were determined by the percent kill of Daudi cells (from human Burkitt lymphoma) by the pre-activated 40 µg/ml of therapeutic agent derived from MC 540 after the activated MC 540 had been stored at the specified temperature and duration of time.

EXAMPLE V

The effect of the duration of treatment on Daudi cells by pre-activated therapeutic agent derived from MC 540 was determined. The activating agent used was 514 nm laser light and the final concentration of the pre-activated therapeutic agent, or drug, was 40 µg/ml. The percent survival of the cancerous Daudi cells was determined by its ability to incorporate $^3$H-alanine as compared to the controls. Data presented in Table 5 show that the pre-activated therapeutic agent had exerted its cytotoxic effect within 30 minutes.

TABLE 5

EFFECT OF THE DURATION OF TREATMENT ON HUMAN BURKITT LYMPHOMA DAUDI CELLS BY PRE-ACTIVATED CHEMOTHERAPEUTIC AGENT DERIVED FROM PHOTOACTIVE COMPOUND MEROCYANINE 540 (MC 540)

| Duration of Treatment In Hours | CPM* Control | CPM* Treated | Percentage Of Survival |
|---|---|---|---|
| 0.1 | 2333 | 342 | 14.7 |
| 1.5 | 1693 | 217 | 12.8 |
| 2.5 | 2835 | 278 | 9.8 |
| 3.5 | 1474 | 166 | 11.2 |
| 5.5 | 1151 | 116 | 10.1 |

*Protein synthesis as determined by incorporation of $^3$H-alanine expressed as counts per minute (CPM).

EXAMPLE VI

The effect of pre-activated therapeutic agent derived from MC 540 upon tumor cells after four hours of treatment was also determined. The pre-activated therapeutic agent was derived from MC 540 activated by 514 nm laser light. Final concentration of the drug was again 40 µg/ml. It is seen from results presented in Table 6 that both tumor cell lines, Daudi and HL-60, were almost totally eradicated even after only four hours of treatment.

TABLE 6

EFFECT OF PRE-ACTIVATED THERAPEUTIC AGENT DERIVED FROM MEROCYANINE 540 (MC 540) UPON TUMOR CELLS AFTER FOUR HOURS OF TREATMENT*

| Cell Type | Control In CPM | Treated In CPM | Percent Kill |
|---|---|---|---|
| Daudi | 30,942 | 4,664 | 84.93 |
| HL-60 | 81,792 | 2,221 | 97.31 |

*Daudi cells, originating from human Burkitt lymphoma, and HL-60 cells, orginating from human leukemia, were treated for 4 hours at 37° C. with 70.2 µM of pre-activated therapeutic agent derived from MC 540. After the treatment period, cells were washed and re-suspended in RPMI-1640 and 10% FBS. Afterward, 0.5/µCi of $^3$H-thymidine was added and the mixture was incubated at 37° C. for overnight. Thymidine incorporation was determined and expressed in counts per minute (CPM).

EXAMPLE VII

The functional activity of normal human bone marrow cells was tested in a granulocyte-macrophage colony formation assay. Methods of assay, such as those disclosed by A. A. Fauser and H. A. Mesner, Blood 53: 1023-27 (1979), were employed, and the disclosure of which is incorporated by reference herein. Briefly, normal bone marrow cells were treated with different final concentrations of pre-activated therapeutic agent derived from MC 540 activated by 514 nm laser light. The mixture was incubated at 37° C. for 24 hours. Afterward, the treated and untreated cells were washed and plated in clonogenic assays. About $1 \times 10^5$ cells were added to each plate containing 1 ml of 0.8% methylcellulose (Methocel A 4M, Dow Chemical Co., Midland, Mich.), 20% of FBS, 0.6 nM of 2-mercaptoethanol, 100 units penicillin/100 µg Streptomycin and 100 µl of recombinant colony stimulating factor (Genzyme, Boston, Maine). Colonies consisting of 30 or more cells were counted on days 10 to 14. Data presented in Table 7 show that with a final concentration of 20 μg/ml of pre-activated therapeutic agent derived from MC 540, about 87% of the colony forming cells survived the treatment, while about 43% of the colony forming cells survived the treatment with the pre-activated therapeutic agent at a final concentration of 40 μg/ml.

TABLE 7
EFFECT OF PRE-ACTIVATED THERAPEUTIC AGENT DERIVED FROM PHOTOACTIVE COMPOUND MEROCYANINE 540 (MC 540) ON GRANULOCYTEMACROPHAGE COLONY FORMATION

| Concentration Of Activated MC 540 In μg/ml | Number Of Colonies | Mean ± S.D.* | Percent Of Untreated Control |
|---|---|---|---|
| 0 | 95, 76, 86 | 85.66 ± 9.50 | 100 |
| 20 | 62, 80, 82 | 74.66 ± 11.01 | 87.7 |
| 40 | 36, 28, 47 | 37 ± 9.54 | 43.2 |

*S.D. = Standard Deviation

EXAMPLE VIII

The effect of pre-activated therapeutic agent derived from MC 540 on the clonogenic tumor stem cell was inventigated. To assay clonogenic tumor stem cells, untreated and treated cells were plated using the procedure described in EXAMPLE VII above, except that no colony stimulating factor was added and colonies consisting of 50 or more cells were counted on day 7. The pre-activated therapeutic agent used in this experiment was derived from MC 540 irradiated with 514 nm laser light. Results presented in Table 8 show that the pre-activated therapeutic agent reduced about 98% of the clonogenic tumor stem cell in all the leukemic and lymphoma cell lines that were tested. For multiple myeloma cells, however, there was only about 35% reduction in the clonogenic tumor stem cell. Hence, multiple myeloma cells were not as sensitive as either leukemic or lymphoma cells toward treatment by pre-activated therapeutic agent derived from MC 540.

TABLE 8
EFFECT OF PRE-ACTIVATED THERAPEUTIC AGENT DERIVED FROM PHOTOACTIVE COMPOUND MEROCYANINE 540 (MC 540) ON CLONOGENIC TUMOR STEM CELLS

| Cell Lines* | Number Of Colonies | | Percentage Reduction Of Colony Formation |
|---|---|---|---|
| | Control | Treated** | |
| Daudi | 452 | 8 | 98.2 |
| HL-60 | 368 | 6 | 98.4 |
| HS-Sultan | 688 | >450 | 34.6 |
| L1210 | 454 | 7 | 98.5 |
| BT-20† | 1500 | 22 | 98.5 |

*With the exception of L1210 cells, which are meurine leukemia cells, all other cells lines originate from human. Daudi cells originate from human Burkitt lymphoma; HL-60 cells originate from human leukemia; HS-Sultan cells originate from human multiple myeloma; and BT-20 cells originate from human breast cancer.
**Concentration of 40 μg/ml was used of the pre-activated therapeutic agent derived from MC 540.
†BT-20 cells were treated with two doses of 80 μg/ml of pre-activated therapeutic agent derived from MC 540 for 24 hours each prior to the clonogenic assays.

EXAMPLE IX

Effect of pre-activated therapeutic agents derived from benzoporphyrin derivatives and Methylene Blue on the survival of tumor cells were determined. Results presented in Table 9 show that of the four Diel-Alder adducts of protoporphyrin tested, the mono-acid derivative of ring A (MAA) yielded the most potent resultant pre-activated therapeutic agent. At a final concentration of 400 ng/ml, it killed about 90% of the Daudi tumor cells, originated from human Butkitt lymphoma.

Data presented in Table 9 show that the pre-activated therapeutic agent derived from Methylene Blue was also a very potent anti-tumor agent. At a final concentration of $10^{-5}M$, it eradicated about 96% of the H-69 tumor cells originated from human small cell lung carcinoma.

TABLE 9
EFFECT OF PRE-ACTIVATED THERAPEUTIC AGENTS DERIVED FROM PHOTOACTIVE COMPOUNDS BENZOPORPHYRIN DERIVATIVES AND METHYLENE BLUE ON TUMOR CELL SURVIVAL

| Cells | Activated Photoactive Compound | Concentration Of Activated Photoactive Compound | % Kill |
|---|---|---|---|
| Daudi | MAA | 50 ng/ml | <10 |
| | | 100 ng/ml | <10 |
| | | 200 ng/ml | 60 |
| | | 400 ng/ml | 90 |
| | MAB | 50 ng/ml | 35 |
| | | 100 ng/ml | 63 |
| | | 200 ng/ml | 30 |
| | | 400 ng/ml | 66 |
| | DAA | 50 ng/ml | <10 |
| | | 100 ng/ml | 20 |
| | | 200 ng/ml | 26 |
| | | 400 ng/ml | 26 |
| | DAB | 50 ng/ml | 7 |
| | | 100 ng/ml | 20 |
| | | 200 ng/ml | 29 |
| | | 400 ng/ml | |
| H 69 | MB | $10^{-4}$ M | 99.8 |
| | | $10^{-5}$ M | 95.8 |

The benzoporphyrin derivatives were synthesized from protoporphyrin and involving the formation of Diel-Alder adducts followed by acid hydrolysis. Four components, mono- and di-acid derivatives of either ring A or ring B fused porphyrins were obtained: Mono-acid derivative of ring A (MAA); mono-acid derivative of ring B (MAB); di-acid derivative of ring A (DAA); and di-acid derivative of ring B (DAB). The methodology has been reported and is hereby incorporated by reference. J. S. Panka, A. R. Morgan, and D. Dolphin, J. Org. Chem. 51:1094-1100 (1986).
The benzoporphyrin derivatives (MAA, MAB, DAA, DAB) were activated by irradiation with 690 nm laser light for 20 minutes at 150 m Watts prior to being brought into contact with cells. Methylene Blue (MB) was activated by exposure to 630 nm laser light for 25 minutes at 200 m Watts prior to being brought into contact with cells. Aliquots of pre-activated photoactive therapeutic agents were added to 1 ml of cells and incubated overnight. The next day, $^3$H-thymidine uptake was carried out and incorporation was determined after 24 hours of incubation.

EXAMPLE X

Effect of pre-activated therapeutic agent derived from benzoporphyrin derivatives on the survival of bone marrow cells was determined. Normal human bone marrow cells were treated with various doses of pre-activated therapeutic agent so prepared, and the viability of cells were determined by Trypan Blue dye exclusion method. It is seen from data presented in Table 10 that these pre-activated agents were relatively non-toxic to normal human bone marrow cells.

TABLE 10
EFFECT OF PRE-ACTIVATED THERAPEUTIC AGENT DERIVED FROM PHOTOACTIVE COMPOUNDS BENZOPORPHYRIN DERIVATIVES ON SURVIVAL OF NORMAL BONE MARROW

| Concentration Of Activated Benzoporphyrin Derivative | Activated Benzoporphyrin Derivative Used - Percent Survival | | | |
|---|---|---|---|---|
| | MMA | MAB | DAA | DAB |
| 50 ng/ml | 79 | 47 | 82 | 98 |
| 100 ng/ml | 68 | 32 | 66 | 86.05 |

TABLE 10-continued

EFFECT OF PRE-ACTIVATED THERAPEUTIC
AGENT DERIVED FROM PHOTOACTIVE
COMPOUNDS BENZOPORPHYRIN DERIVATIVES
ON SURVIVAL OF NORMAL BONE MARROW

| Concentration Of Activated Benzoporphyrin Derivative | Activated Benzoporphyrin Derivative Used - Percent Survival | | | |
|---|---|---|---|---|
| | MMA | MAB | DAA | DAB |
| 200 ng/ml | 46 | 22 | 58 | 73.27 |

The benzoporphyrin derivatives used herein are listed in TABLE 9.
Activation of benzoporphyrin derivative was accomplished by irradiation with 690 nm laser light at 150 m Watts for 20 minutes prior to being brought into contact with cells. Bone marrow cells were treated with various doses of activated benzoporphyrin derivatives and viability of cells determined.

EXAMPLE XI

The toxicity of cytoxicity of benzoporphyrin derivatives to normal bone marrow cells in the dark was determined. This experiment was performed to determine the inherent toxicity of benzoporphyrin derivatives. The viability of the bone marrow cells was assayed by the method of Trypan Blue dye exclusion method. Results presented in Table 11 show that the three benzoporphyrin derivatives tested, namely, the mono-acid derivative of ring A (MAA), mono-acid derivative of ring B (MAB), and the di-acid derivative of ring B (DAB), were relatively not cytotoxic to normal human bone marrow cells. The di-acid derivative of ring B (DAB) was the least cytotoxic of the three.

TABLE 11

TOXICITY OF BENZOPORPHYRIN DERIVATIVES
TO NORMAL HUMAN BONE MARROW CELLS IN
THE DARK

| Concentration Of Benzoporphyrin Derivative | Benzoporphyrin Derivative Used Percent Viability Of Bone Marrow Cells | | | |
|---|---|---|---|---|
| | MMA | MAB | DAA | DAB |
| 200 ng/ml | 48 | 67 | N.D.* | 83 |

The benzoporphyrin derivatives used herein are given in TABLE 9.
Bone marrow cells were incubated in the dark for overnight with desired concentrations of the benzoporphyrin derivatives and viability was determined after 24 hour incubation.
*N.D. = Not determined.

EXAMPLE XII

The therapeutic properties of the pre-activated therapeutic agent and the "post-activated" MC 540 were compared. The pre-activated therapeutic agent was prepared in the usual manner in that the activation of the MC 540 with 514 nm laser light was accomplished prior to the pre-activated agent was brought into contact with either normal cells or tumor cells. In the "post-activation" experiment, similar cells were exposed to both MC 540 and 514 nm laser light simultaneously for 24 hours. Hence, in the pre-activation experiment, the activating agent, the laser light, was absent when cells were treated with the pre-activated therapeutic agent derived from MC 540. In contrast, in the "post-activation" experiment, the activating agent, the laser light, was present when cells were treated with MC 540.

Data presented in Table 12 show that the therapeutic efficacy of the "post-activated" MC 540 and the pre-activated therapeutic agent derived from MC 540 was very similar. Both agents showed low cytotoxicity toward normal cells, yet they both exhibited high cytotoxicity toward human tumor cells.

TABLE 12

COMPARISON OF THE EFFECT OF PRE-
ACTIVATED THERAPEUTIC AGENT DERIVED
FROM MEROCYANINE 540 (MC 540) AND
POST-ACTIVATED MC 540 ON CELL CYTOTOXICITY

| Cell Type[3] | Pre-activation[1] | | Post-Activation[2] | | |
|---|---|---|---|---|---|
| | Concentration Of Activated MC 540 In μM | % Kill | Concentration Of MC 540 In μM | Light Energy Density In J/cm$^2$ | % Kill |
| PBL[4] | 70.2 | 10 | 35.1 | 93.6 | 10.0 |
| PBL[5] | 70.2 | 10 | 35.1 | 93.6 | N.D. |
| Daudi[6] | 70.2 | 96 | 35.1 | 93.6 | 99.99 |
| Daudi[6] | 140.4 | 99 | 35.1 | — | 6 |
| Daudi[6] | — | — | — | 36.2 | 18 |
| HL-60[6] | 70.2 | 98 | 35.1 | 93.6 | 99.99 |
| HL-60[6] | — | — | 35.1 | — | 8 |
| HL-60[6] | — | — | — | 93.6 | 20 |

[1]In the pre-activated experiment, the pre-activated therapeutic agent was derived from MC 540 by irradiating MC 540 with 514 nm laser light for about 15 minutes prior to being brought into contact with cells. Cells were treated with pre-activated therapeutic agent derived from MC 540 for 24 hours.
[2]In the post-activated experiment, cells were exposed to both MC 540 and laser light at 514 nm simultaneously for 24 hours.
[3]PBL = Normal human peripheral blood lymphocytes. Daudi cells originated from human Burkitt lymphoma. HL-60 cells originated from human leukemia.
[4]Cell kill was determined by Trypan Blue dye exclusion method.
[5]Cells were stimulated with phytohemaglutinin (PHA) before addition of $^3$H-thymidine. Cell kill was determined by $^3$H-thymidine incorporation method.
[6]Cell kill was determined by $^3$H-thymidine incorporation method.

EXAMPLE XIII

Effect of buthinine sulfoximine (BSO), a chemomodifying agent, on the therapeutic efficacy of pre-activated therapeutic agent derived from MC 540 was determined. Results in Table 1 have shown that tumor cells originating from human multiple myeloma were not very sensitive to the action of the pre-activated therapeutic agent derived from MC 540 activated by 514 nm laser light. Yet, results collected in Table 13 clearly show that BSO, which was non-toxic to the tumor cells by itself, significantly enhanced or synergized the therapeutic activity of the pre-activated therapeutic agent derived from MC 540. After being pre-treated with BSO, tumor cells, which were initially not very sensitive to pre-activated therapeutic agent derived from MC 540, were almost totally eradicated by the same pre-activated therapeutic agent.

TABLE 13

EFFECT OF CHEMOMODIFYING AGENT,
BUTHIONINE SULFOXIMINE (BSO), ON
THE KILLING OF MYELOMA CELLS BY
PRE-ACTIVATED THERAPEUTIC AGENT
DERIVED FROM MEROCYANINE 540 (MC 540)

| Cells | Concentration Of BSO In mg/ml | Concentration Of Activated MC 540 In μg/ml | % Kill |
|---|---|---|---|
| HS-Sultan (control) | — | — | 0 |
| HS-Sultan | — | 40 | 31 |
| HS-Sultan | 1 | — | 0 |
| HS-Sultan | 1 | 40 | 99.7 |
| ARH 77 (control) | — | — | 0 |
| ARH 77 | — | 40 | 0 |
| ARH 77 | 1 | — | 0 |
| ARH 77 | 1 | 40 | >99 |

Cells were first treated with BSO for 2 hours. They were then washed and re-suspended in growth medium. The pre-activated therapeutic agent derived from MC 540 was then added and the mixture was incubated overnight at 37° C. Cell kill was determined by $^3$H-thymidine incorporation.

EXAMPLE XIV

Pre-activated therapeutic agent derived from either MC 540 or DEH, both irradiated with laser light, also exhibited anti-viral properties. Herpes simplex Type I (MacIntyre strain) and vesicular somatitis (VSV) strain was used for the experiment. Different concentrations of the pre-activated therapeutic agent was added to the cell free viral suspensions. Both the treated and control virus suspensions were incubated at 37° C. After 24 hours of incubation, aliquots of virus suspensions were inoculated for plaque forming assay. The plaque forming units were counted on day five. Methods of viral studies, such as those disclosed by N. J. Schmidt, In: E. H. Lennette and J. J. Schmidt, eds. Diagnostic Procedures For Viral, Rickettsial And Chlamydial Infections. 5th ed. Washington, D.C. American Public health Association, 1979: 104–110, were employed, and the disclosure of which is incorporated by reference herein.

Results presented in Table 14 show that the pre-activated therapeutic agent, derived either from MC 540 or from DHE, was an effective anti-viral agent.

TABLE 14

EFFECT OF PRE-ACTIVATED THERAPEUTIC AGENTS DERIVED FROM PHOTOACTIVE COMPOUNDS, MEROCYANINE 540 (MC 540) AND DIHEMATOPORPHYRIN ETHER (DHE) ON HERPES SIMPLEX VIRUS TYPE I

| Activated Photoactive Compound (Concentration In μg/ml) | PFU†/ml | % Kill Of Virus |
|---|---|---|
| Untreated Control (0) | $1 \times 10^5$ | 0 |
| MC 540* (80) | $<1 \times 10^2$ | >99.9 |
| MC 540* (120) | $<1 \times 10^2$ | >99.9 |
| DHE* (25) | $1 \times 10^4$ | 90.0 |
| DHE* (50) | $1 \times 10^2$ | 99.9 |

†PFU = Plaque forming unit.
*Pre-activated therapeutic agent derived from the photoactive compound

EXAMPLE XV

Effect of pre-activated therapeutic agent derived from MC 540 activated by 514 nm laser light on *E. coli* was determined. Results tabulated in Table 15 show that the pre-activated therapeutic agent so prepared was also a rather effective anti-bacterial agent.

TABLE 15

EFFECT OF PRE-ACTIVATED THERAPEUTIC AGENT DERIVED FROM MEROCYANINE 540 (MC 540) ON *E. COLI* (ATCC 25992)

| Concentration Of Activated MC 540 In μg/ml | Average Number Of Colonies | % Kill |
|---|---|---|
| 0* | 62.13 | 0 |
| 40* | 35.57 | 57.25 |
| 0** | 396 | 0 |
| 80** | 224 | 56.56 |

*E. coli suspension was incubated either in the presence or absence of pre-activated therapeutic agent derived from MC 540 in phosphate buffered saline at 37° C. for 22 hours. After the incubation period, an aliquot of E. coli suspension was plated in triplicate for cell growth. Colonies were counted after 24 hours at 37° C. The number given is an average of triplicate counts.
**E. coli suspension was incubated either in the presence or absence of pre-activated therapeutic agent derived from MC 540 in trypticase soy broth at 37° C. for 8 hours. After the incubation period, aliquots were plated on blood agar plates. Colonies were counted after overnight incubation. The number given is an average of triplicate counts.

From the above examples and tables, it is apparent that the invention has produced effective pre-activated therapeutic agents derived from a photoactive compounds. The present invention has also provided efficient methods for the preparation of these pre-activated therapeutic agents or mixtures. These pre-activated therapeutic agents were shown to be relatively non-toxic to normal human cells, yet they killed tumor cells and other pathogenic biological contaminants readily. The present invention also has produced methods for treating body tissues, which are infected with tumors or other pathogenic biological contaminants, either inside or outside the animal body.

While the present invention has been particularly described in terms of specific embodiments thereof, it will be understood in view of the present disclosure that numerous variations upon the invention are now enabled to those skilled in the art, which variations yet reside within the scope of the present invention. Accordingly, the invention is to be broadly construed, and limited only by the scope and spirit of the claims now appended hereto.

We claim:

1. A pre-activated therapeutic agent comprising:
   (a) a pharmaceutically acceptable carrier;
   (b) a photoactive compound dissolved in said pharmaceutically acceptable carrier producing a resultant solution, said photoactive compound being characterized in that it has at least one chromophore and that it is susceptible to activation by an activating agent; and
   (c) said resultant solution being subjected to a sufficient amount of activating agent prior to being brought into contact with body tissue to be treated such that the photoactive compound is activated to produce a resultant therapeutic mixture, said therapeutic mixture being characterized in that, subsequent to activation, it has preferential affinity toward tumors or other pathogenic biological contaminants infecting said body tissue; that, subsequent to activation, it is capable of interacting with, and destroying, tumors or other pathogenic biological contaminants infecting said body tissue by contact therewith; that, subsequent to activation, it is, at effective dosages, relatively non-toxic to normal tissues or normal cells; and that its therapeutic properties are retained for at least a time sufficient to destroy said tumors or other pathogenic biological contaminants subsequent to activation.

2. A pre-activated therapeutic agent in accordance with claim 1 wherein said photoactive compound is selected from the group consisting of porphyrin, oxazine, thiazine, and cyanine.

3. A pre-activated therapeutic agent in accordance with claim 1 wherein said activating agent is selected from the group consisting of radiation energy, electromagnetic energy, and electrical energy.

4. A pre-activated therapeutic agent in accordance with claim 3 wherein said electromagnetic energy is selected from the group consisting of white light, ultraviolet light, gamma rays, and lasers.

5. A pre-activated therapeutic agent in accordance with claim 1 wherein said activating agent is a chemical compound capable of activating said photoactive compound.

6. A pre-activated therapeutic agent comprising:
   (a) a pharmaceutically acceptable carrier;
   (b) a photoactive compound dissolved in said pharmaceutically acceptable carrier producing a resultant solution, said photoactive compound being characterized in that it has at least one chromophore and that it is susceptible to activation by electromagnetic energy; and (c) said resultant solution being subjected to a sufficient amount of electromagnetic energy prior to being brought into contact with body tissue to be treated such that the photoactive compound is activated to produce a resultant therapeutic mixture, said therapeutic mixture being characterized in that, subsequent to activation, it has preferential affinity toward tumors or other pathogenic biological contaminants infecting said body tissue; that, subsequent to activation, it is capable of interacting with, and destroying, tumors or other pathogenic biological contaminants infecting said body tissue by contact therewith; that, subsequent to activation, it is, at effective dosages, relatively non-toxic to normal tissues or normal cells, and that its therapeutic properties are retained for at least a time sufficient to destroy said tumors or other pathogenic biological contaminants subsequent to activation.

7. A pre-activated therapeutic agent in accordance with claim 6 wherein said photoactive compound is selected from the group consisting of porphyrin, oxazine, thiazine, and cyanine.

8. A pre-activated therapeutic agent in accordance with claim 7 wherein said electromagnetic energy has a wavelength range of from about 350 nm to about 750 nm and an energy density from about $0.1 \text{ J/cm}^2$ to about $3000 \text{ J/cm}^2$.

9. A pre-activated therapeutic agent comprising:
(a) a pharmaceutically acceptable carrier;
(b) a photoactive compound dissolved in said pharmaceutically acceptable carrier producing a resultant solution, said photoactive compound being characterized in that it has at least one chromophore and that it is susceptible to activation by an activating agent;
(c) said resultant solution being subjected to a sufficient amount of activating agent prior to being brought into contact with body tissue to be treated such that the photoactive compound is activated to produce a resultant therapeutic mixture, said therapeutic mixture being characterized in that, subsequent to activation, it has preferential affinity toward tumors or other pathogenic biological contaminants infecting said body tissue; that, subsequent to activation, it is capable of interacting with, and destroying, tumors or other pathogenic biological contaminants infecting said body tissue by contact therewith; that, subsequent to activation, it is, at effective dosages, relatively non-toxic to normal tissues or normal cells, and that its therapeutic properties are retained for at least a time sufficient to destroy said tumors or other pathogenic biological contaminants subsequent to activation; and
(d) a chemomodifying agent added to said resultant therapeutic mixture, said chemomodifying agent being characterized in that it is, at effective dosages, relatively non-toxic to normal tissues or normal cells and that it can augment the therapeutic effect of said resultant therapeutic mixture.

10. A pre-activated therapeutic agent in accordance with claim 9 wherein said photoactive compound is selected from the group consisting of porphyrin, oxazine, thiazine, and cyanine.

11. A pre-activated therapeutic agent in accordance with claim 9 wherein said activating agent is selected from the group consisting of radiation energy, electromagnetic energy, and electrical energy.

12. A pre-activated therapeutic agent in accordance with claim 11 wherein said electromagnetic energy is selected from the group consisting of white light, ultraviolet light, gamma rays, and lasers.

13. A pre-activated therapeutic agent in accordance with claim 9 wherein said chemomodifying agent is buthionine sulfoximine.

14. A therapeutic agent produced by a method comprising
(a) dissolving dihematoporphyrin ether in a pharmaceutically acceptable carrier to produce a resultant solution; and
(b) subjecting said resultant solution to a sufficient amount of irradiation in the wavelength of from about 300 nm to about 700 nm prior to being brought into contact with body tissue to be treated such that
the dihematoporphyrin ether is activated to produce a resultant therapeutic mixture, and the therapeutic mixture being characterized in that subsequent to activation, it is capable of interacting with, and destroying, tumors or other pathogenic biological contaminants infecting the body tissue by contact therewith,
subsequent to activation it is, at effective dosages, relatively non-toxic to normal tissue or normal cells, and
its therapeutic properties are retained for at least about 10 seconds at room temperature subsequent to activation.

15. A therapeutic agent produced by a method comprising
(a) dissolving n,n$^1$-bis(2-ethyl-1,3-dioxolane)-kryptocyanine in a pharmaceutically acceptable carrier to produce a resultant solution; and
(b) subjecting the resultant solution to a sufficient amount of irradiation of a wavelength of about 550 to 800 nm prior to contacting it with a body tissue to be treated such that the N,N'-bis(2-ethyl-1,3-dioxolane)-kryptocyanine is activated to produce a therapeutic mixture, the therapeutic mixture being characterized in that
subsequent to activation it is capable of interacting with, and destroying, tumors or other pathogenic biological contaminants infecting the body tissue by contact therewith,
subsequent to activation it is, at effective dosages, relatively non-toxic to normal tissue or normal cells, and
its therapeutic properties are retained for at least about 10 seconds at room temperature subsequent to activation.

16. A therapeutic agent produced by a method comprising
(a) dissolving methylene blue in a pharmaceutically acceptable carrier to produce a resultant solution; and
(b) subjecting the resultant solution to a sufficient amount of irradiation of a wavelength of about 5450 to 800 nm prior to contacting it with body tissue to be treated such that the methylene blue is activated to produce a resultant therapeutic mixture, the therapeutic mixture being characterized in that
subsequent to activation it is capable of interacting with, and destroying, tumors or other pathogenic biological contaminants infecting said body tissue by contact therewith, subsequent to activation it is, at effective dosages, relatively non-toxic to normal tissue or normal cells, and its therapeutic properties are retained for at least about 10 seconds at room temperature subsequent to activation.

17. A therapeutic agent produced by a method comprising
- (a) dissolving a mono-acid derivative of a ring A fused porphyrin derived from a Diel-Alder adduct in a pharmaceutically acceptable carrier to produce a resultant solution; and
- (b) subjecting the resultant solution to a sufficient amount of irradiation of a wavelength of about 400 to 750 nm prior to contacting it with body tissue to be treated such that the mono-acid derivative of ring A fused porphyrin derived from a Diel-Alder adduct is activated to produce a resultant therapeutic mixture, the therapeutic mixture being characterized in that subsequent to activation it is capable of interacting with, and destroying, tumors or other pathogenic biological contaminants infecting said body tissue by contact therewith, subsequent to activation it is, at effective dosages, relatively non-toxic to normal tissue or normal cells, and its therapeutic properties are retained for at least about 10 seconds at room temperature subsequent to activation.

18. A pre-activated therapeutic agent in accordance with claim 2 wherein said porphyrin is selected from the group consisting of dihematoporphyrin ether, benzoporphyrin, metalloporphyrin, and mono-acid derivative of ring A fused porphyrin derived from Diel-Alder adduct.

19. A pre-activated therapeutic agent in accordance with claim 2 wherein said cyanine comprises Merocyanine 540.

20. A pre-activated therapeutic agent in accordance with claim 2 wherein said thiazine comprises Methylene Blue.

21. A pre-activated therapeutic agent in accordance with claim 2 wherein said cyanine comprises N,N'-bis(2-ethyl-1,3-dioxolane)kryptocyanine.

22. A pre-activated therapeutic agent in accordance with claim 7 wherein said porphyrin is selected from the group consisting of dihematoporphyrin ether, benzoporphyrin, metalloporphyrin, and mono-acid derivative of ring A fused porphyrin derived from Diel-Alder adduct.

23. A pre-activated therapeutic agent in accordance with claim 7 wherein said cyanine comprises Merocyanine 540.

24. A pre-activated therapeutic agent in accordance with claim 7 wherein said thiazine comprises Methylene Blue.

25. A pre-activated therapeutic agent in accordance with claim 7 wherein said cyanine comprises N,N'-bis(2-ethyl-1,3-dioxolane)kryptocyanine.

26. A pre-activated therapeutic agent in accordance with claim 10 wherein said porphyrin is selected from the group consisting of dihematoporphyrin ether, benzoporphyrin, metalloporphyrin, and mono-acid derivative of ring A fused porphyrin derived from Diel-Alder adduct.

27. A pre-activated therapeutic agent in accordance with claim 10 wherein said cyanine comprises Merocyanine 540.

28. A pre-activated therapeutic agent in accordance with claim 10 wherein said thiazine comprises Methylene Blue.

29. A pre-activated therapeutic agent in accordance with claim 10 wherein said cyanine comprises N,N'-bis(2-ethyl-1,3-dioxolane)kryptocyanine.

30. A pre-activated therapeutic agent comprising:
- (a) a pharmaceutically acceptable carrier;
- (b) a porphyrin compound dissolved in said pharmaceutically acceptable carrier producing a resultant solution; and
- (c) said resultant solution being subjected to a sufficient amount of activating agent prior to being brought into contact with body tissue to be treated such that said porphyrin compound is activated to produce a resultant therapeutic mixture, said therapeutic mixture being characterized in that subsequent to activation, it is capable of interacting with, and destroying, tumors or other pathogenic biological contaminants infecting said body tissue by contact therewith; that, subsequent to activation, it is, at effective dosages, relatively non-toxic to normal tissues or normal cells; and that its therapeutic properties are retained for at least a time sufficient to destroy said tumors, viruses or other pathogenic biological contaminants.

31. A pre-activated therapeutic agent in accordance with claim 30, wherein said porphyrin compound is selected from the group consisting of dihematoporphyrin ether and benzoporphyrin derivative.

32. A pre-activated therapeutic agent comprising:
- (a) a pharmaceutically acceptable carrier;
- (b) a thiazine compound dissolved in said pharmaceutically acceptable carrier producing a resultant solution; and
- (c) said resultant solution being subjected to a sufficient amount of activating agent prior to being brought into contact with body tissue to be treated such that said thiazine compound is activated to produce a resultant therapeutic mixture, said therapeutic mixture being characterized in that subsequent to activation, it is capable of interacting with, and destroying, tumors or other pathogenic biological contaminants infecting said body tissue by contact therewith; that, subsequent to activation, it is, at effective dosages, relatively non-toxic to normal tissues or normal cells; and that its therapeutic properties are retained for at least a time sufficient to destroy said tumors, viruses or other pathogenic biological contaminants.

33. A pre-activated therapeutic agent in accordance with claim 32, wherein said thiazine compound comprises Methylene Blue.

34. A pre-activated therapeutic agent comprising:
- (a) a pharmaceutically acceptable carrier;
- (b) a cyanine compound dissolved in said pharmaceutically acceptable carrier producing a resultant solution; and
- (c) said resultant solution being subjected to a sufficient amount of activating agent prior to being brought into contact with body tissue to be treated such that said cyanine compound is activated to produce a resultant therapeutic mixture, said therapeutic mixture being characterized in that subsequent to activation, it is capable of interacting with, and destroying, tumors or other pathogenic biological contaminants infecting said body tissue by contact therewith; that, subsequent to activation, it is, at effective dosages, relatively non-toxic to normal tissues or normal cells; and that its therapeutic properties are retained for at least a time sufficient to destroy said tumors, viruses or other pathogenic biological contaminants.

35. A pre-activated therapeutic agent in accordance with claim 34, wherein said cyanine compound is selected from the group consisting of Merocyanine 540 and N,N'-bis(2-ethyl-1,3-dioxolane)kryptocyanine.

* * * * *

UNITED STATES PATENT AND TRADEMARK OFFICE
CERTIFICATE OF CORRECTION

PATENT NO. : 5,091,385
DATED : February 25, 1992
INVENTOR(S) : Gulliya, et al.

It is certified that error appears in the above-identified patent and that said Letters Patent is hereby corrected as shown below:

Claim 16, column 26, line 62, cancel "5450" and substitute -- 550 --.

Signed and Sealed this

Fourteenth Day of September, 1993

Attest:

BRUCE LEHMAN

*Attesting Officer*     *Commissioner of Patents and Trademarks*